United States Patent [19]

Friese et al.

[11] Patent Number: 5,474,665
[45] Date of Patent: Dec. 12, 1995

[54] MEASURING SENSOR FOR DETERMINING THE OXYGEN CONTENT OF GAS MIXTURES

[75] Inventors: Karl-Hermann Friese, Leonberg; Hermann Dietz, Gerlingen; Hermann Fischer, Stuttgart; Manfred Koeder; Werner Gruenwald, both of Gerlingen; Ulrich Eisele, Stuttgart, all of Germany

[73] Assignee: Robert Bosch GmbH, Stuttgart, Germany

[21] Appl. No.: 306,572

[22] Filed: Sep. 15, 1994

[30] Foreign Application Priority Data

Sep. 30, 1993 [DE] Germany .................... 43 33 232.3

[51] Int. Cl.[6] .................................................. G01N 27/407
[52] U.S. Cl. .................... 204/153.18; 204/425; 204/426; 204/427
[58] Field of Search .................... 204/153.18, 421–429

[56] References Cited

U.S. PATENT DOCUMENTS

| | | | |
|---|---|---|---|
| 3,841,987 | 10/1974 | Friese et al. | 204/427 |
| 4,127,464 | 11/1978 | Ichikawa et al. | 204/428 |
| 4,200,511 | 4/1980 | Sato et al. | 204/428 |
| 4,277,323 | 7/1981 | Muller et al. | 204/425 |
| 4,765,880 | 8/1988 | Hayakawa et al. | 204/425 |
| 4,839,019 | 6/1989 | Takahama et al. | 204/426 |
| 4,909,922 | 3/1990 | Kato et al. | 204/425 |
| 5,290,421 | 3/1994 | Reynolds et al. | 204/424 |

*Primary Examiner*—T. Tung
*Attorney, Agent, or Firm*—Spencer, Frank & Schneider

[57] ABSTRACT

The invention relates to a measuring sensor having pump reference for measuring the oxygen content of gas mixtures, particularly exhaust gases of internal combustion engines. The sensor includes a measuring cell (A) and a reference cell (B) each having a pair of electrodes, with one of each respective pairs of electrodes being common to the two cells, and having a fixed electrolyte. Reference cell (B) has defined therein an internal oxygen reference zone which is hermetically sealed from the gas mixture and which is connected to the atmosphere by way of a pressure-equalization line. The measuring cell (A) and the reference cell (B) can be heated by heating apparatus to a temperature at which the fixed electrolyte has an ionic conductivity which is sufficiently high. The heating apparatus and a porous insulation are advantageously disposed in the vicinity of the electrode of the reference cell which is not in common with the measuring cell and which is porous so that the porous insulation, together with the porous electrode, form the internal oxygen reference zone and, together with the porous electrode and its porous conductor track, form the pressure-equalization line.

9 Claims, 4 Drawing Sheets

MEASURING SENSOR FOR DETERMINING THE OXYGEN CONTENT OF GAS MIXTURES

CROSS-REFERENCE TO RELATED APPLICATIONS

The present application claims the right of foreign priority with respect to Application No. P 43 33 232.3 filed in Germany on Sep. 30, 1993, the subject matter of which is incorporated herein by reference.

BACKGROUND OF THE INVENTION

1. Field of the Invention

The invention relates to a measuring sensor having a pump cell reference for determining the oxygen content of gas mixtures, particularly the oxygen content of exhaust gases of internal combustion engines, in the lean, neutral and rich ranges. The invention further relates to use of the novel measuring sensor to control the oxygen content of the composition of the fuel-air mixture being supplied to an internal combustion engine.

2. Description of the Invention

It is known that, depending on the desired operating state, internal combustion engines, such as diesel and Otto engines, can be operated with fuel/air ratios in which (1) the fuel constituent is present in a stoichiometric surplus (rich range), (2) the oxygen of the air constituent is stoichiometrically predominant (lean range), and (3) the fuel and air constituents satisfy stoichiometric requirements. The composition of the fuel-air mixture determines the composition of the exhaust gas. In the rich range, considerable quantities of nonburned or partially-burned fuel are found, while the oxygen has been substantially consumed and has nearly disappeared. In the lean range, the ratios are reversed, and in a stoichiometric composition of the fuel-air mixture, both fuel and oxygen are minimized. A conventional measure of the fuel/air ratio is the lambda value measured for the exhaust gas, which is >1 in the lean range, <1 in the rich range, and equal to one in the neutral range.

Knowledge of the composition of the exhaust gas is the basis for controlling interventions whose objective is to correspondingly optimizing the fuel-air mixture with regard to the respective requirements. For many years, sensors have been known that measure the oxygen content of exhaust gas and transmit the measuring signal to an evaluation circuit that controls the fuel/air ratio corresponding to the respective requirements. These sensors can operate potentiometrically or polarographically. Potentiometric sensors are based on measuring the voltage between two electrodes under different partial pressures of the gas to be determined. Polarographic sensors are based on measuring the limiting current of a pump cell.

A sensor for controlling the fuel-air mixture for internal combustion engines is known from Federal Republic of Germany Published Application No. 3,632,456. The sensor according to this reference has a first pump cell which has two porous electrodes disposed on opposite sides of a first plate made of a fixed electrolyte that conducts oxygen ions, and a second pump cell which likewise has two porous electrodes which, again, are disposed on opposites sides of a second plate of a fixed, oxygen-conducting electrolyte. One porous electrode of each of the two pump cells is in contact with a gas chamber located between the pump cells, which, for its part, is connected by way of a channel acting as a diffusion-limiting element or throttling element to the gas to be measured. One of the porous electrodes of the first pump cell, which is not the electrode in contact with the gas chamber, simultaneously serves as an internal oxygen reference point. This electrode is connected by way of a leakage throttle element to the other electrode of the first pump cell, which electrode is in contact with the gas chamber. In a specific embodiment, the two electrodes in contact with the gas chamber can be combined into a single electrode.

Such a prior art sensor, however, is complicated to produce and reliable operation over a long period of time could be improved.

Accordingly, it is an object of the present invention to provide a measuring sensor for determining oxygen content of gas mixtures which is more easily produced than prior art sensors of this type and which provides reliable operation over a long period of time with desirably high sensitivity.

SUMMARY OF THE INVENTION

These and other objects are accomplished by the present invention which provides a measuring sensor for determining the oxygen content in a gas mixture including an exhaust gas mixture from an internal combustion engine, including an electrochemical measuring cell (A) having a pair of electrodes; an electrochemical reference cell (B) having a pair of electrodes, one of which pair of electrodes is common to the electrochemical reference cell (B) and the electrochemical measuring cell (A), and having defined therein an internal oxygen reference zone which is hermetically sealed against the gas mixture and is connected to the atmosphere by way of a pressure-equalization line; a diffusion barrier which impedes the diffusion of the gas mixture to the electrode which is common to the electrochemical reference cell (B) and the electro-chemical measuring cell (A); a fixed electrolyte provided between the electrochemical measuring cell (A) and the electrochemical reference cell (B), and a heating means for heating the electrochemical measuring cell (A) and the electrochemical reference cell (B) to a temperature at which the fixed electrolyte has an ionic conductivity effective to enable the measuring sensor to determine the oxygen content in the gas mixture.

The measuring sensor may further comprise a control circuit which includes a voltage source which supplies a supply voltage ($U_V$); a current source which maintains a constant pumping current ($I_P$) in the electrochemical reference cell (B); a reference voltage source which can be set at a reference voltage ($U_R$) which is specific and constant; and an operational amplifier which compares a pumping voltage ($U_P$) present between the pair of electrodes of the electrochemical reference cell (B) with the reference voltage ($U_R$), and which is connected to the electrodes of the electrochemical measuring cell (A) and the electrochemical reference cell (B).

The measuring sensor may advantageously feature a porous conductor track which is in communication with the atmosphere and which is in communication with the internal oxygen reference zone so that the internal oxygen reference zone and the porous conductor track together form the pressure-equalization line.

Preferably, the measuring sensor features an electrode of the electrochemical reference cell (B), which is not in common with the pair of electrodes of the electrochemical measuring cell (A), and which is porous, and the pores thereof define the internal oxygen reference zone. Preferably, the measuring sensor features porous insulation disposed in the vicinity of the porous electrode and the heating means is imbedded in the porous insulation which forms, together with the porous electrode, the internal oxygen reference zone and, together with the porous electrode and the porous conductor track, forms the pressure-equalization line. The porous insulation may be composed of, for example, aluminum oxide.

The fixed electrolyte of the electrochemical measuring cell (A) and the electrochemical reference cell (B) may be composed of, for example, zirconium(IV) oxide which is at least partially stabilized.

The invention additionally contemplates an improved internal combustion engine which includes the foregoing measuring sensor for determining the oxygen content of exhaust gas mixtures from the internal combustion engine whereby the fuel-air mixture's composition being supplied to the internal combustion engine is controlled in response to the oxygen content measured by the measuring sensor.

The invention additionally includes use of the foregoing measuring sensor for controlling a fuel-air mixture's composition being supplied to an internal combustion engine. Thus, an internal combustion engine is provided with a measuring sensor for determining the oxygen content of exhaust gas mixtures from the internal combustion engine; and the fuel-air mixture's composition being supplied to the internal combustion engine is controlled in response to the oxygen content measured by the measuring sensor. Preferably, the reference voltage ($U_R$) is set at a value of about 400 mV.

BRIEF DESCRIPTION OF THE DRAWINGS

The invention is further described by the accompanying Figures in which.

DESCRIPTION OF THE PREFERRED EMBODIMENTS

The measuring sensors having pump cell reference according to the present invention are favorable with respect to production technology, display the desired high sensitivity when used for controlling the composition of the fuel-air mixture supplied to an internal combustion engine, and operate reliably over long periods of time. The pressure-equalization connection from the oxygen reference zone to the atmosphere contributes to this. It prevents reducing components from diffusing out of the gas mixture, such as exhaust gases of an internal combustion engine, into the oxygen reference zone. The danger of such diffusion is present because the oxygen partial pressure at the oxygen reference electrode cannot lead to a convection current in the pressure-equalization connection due to the low pump flow. The circuit arrangement is clearly simpler compared to the one disclosed in Federal Republic of Germany Published Application No. 3,632,456. In terms of production technology, the embodiment of measuring sensor according to the present invention, in which the heating means and oxygen reference cell are spatially and functionally combined, is particularly elegant.

Figure 1:
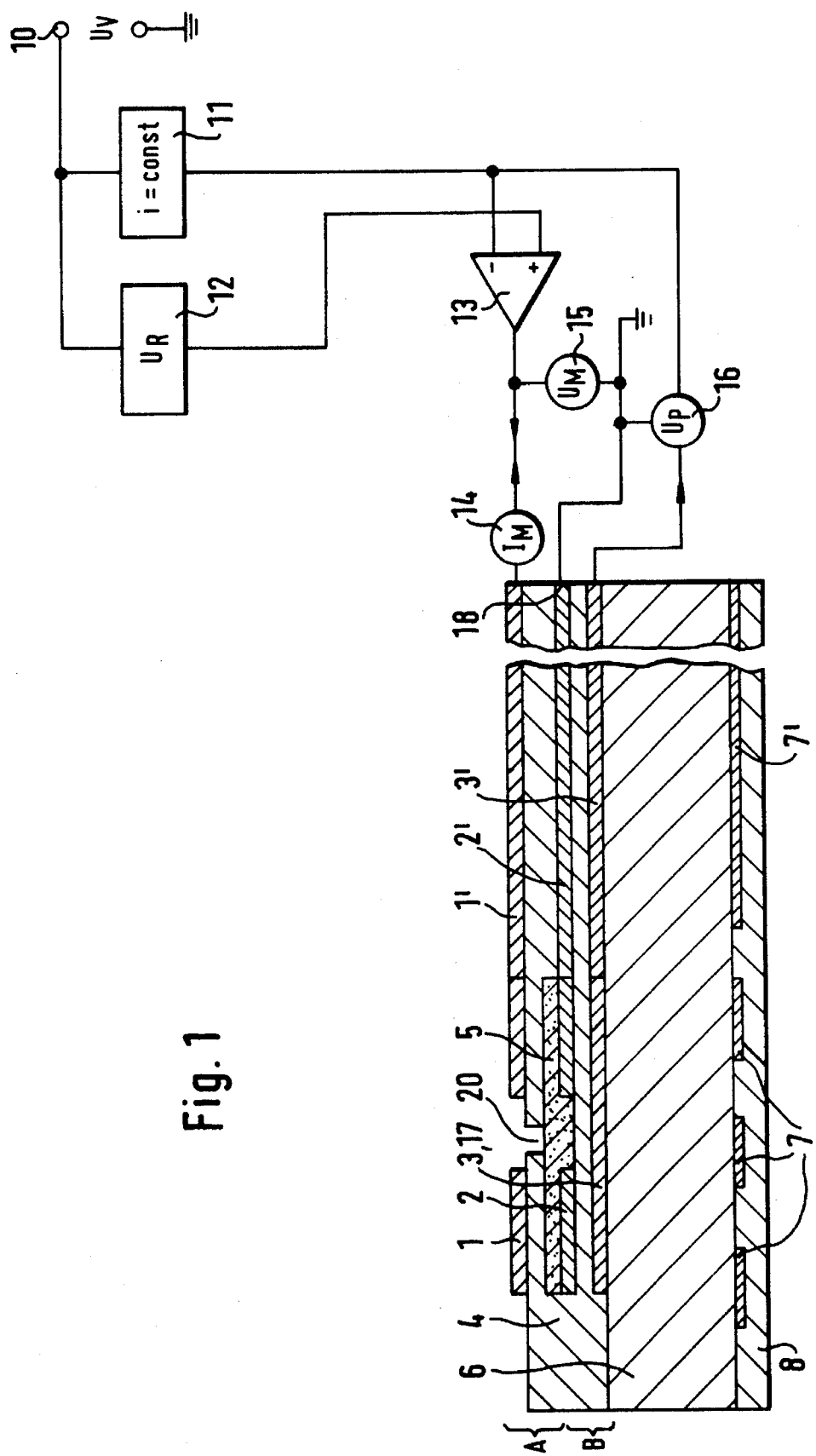
FIG. 1 shows a longitudinal section of an embodiment of a measuring sensor according to the invention, including a schematic representation of a control circuit.
Figure 4:
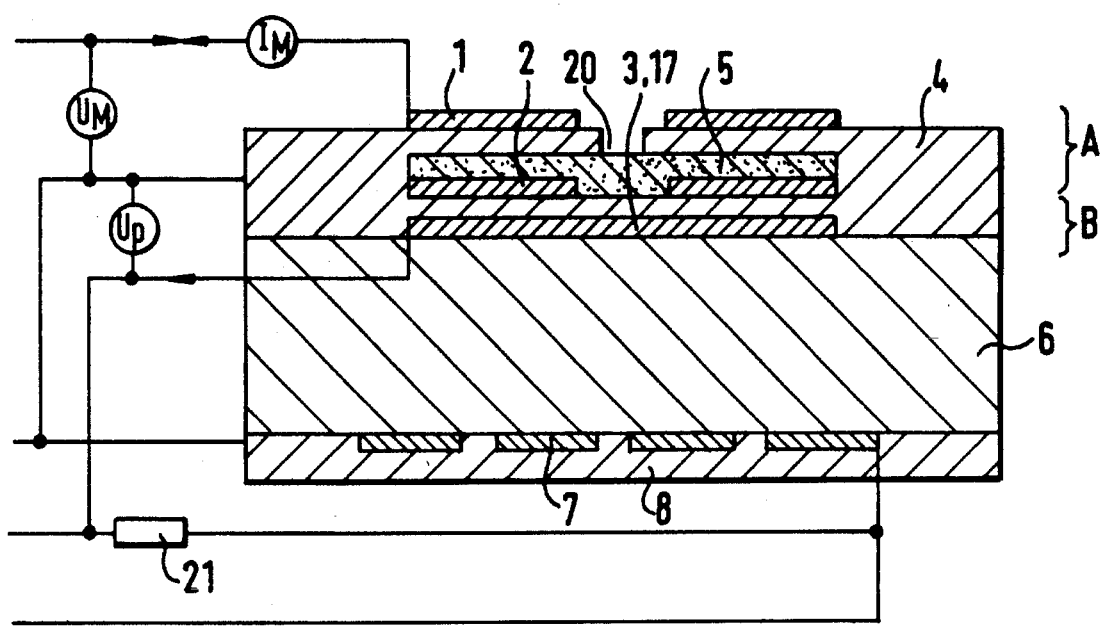
FIG. 4 shows a cross-section of another embodiment of a measuring sensor according to the invention in which the number of connections is reduced. Here the control circuit, which substantially corresponds to that shown in FIG. 1, is not shown.
Figure 5:
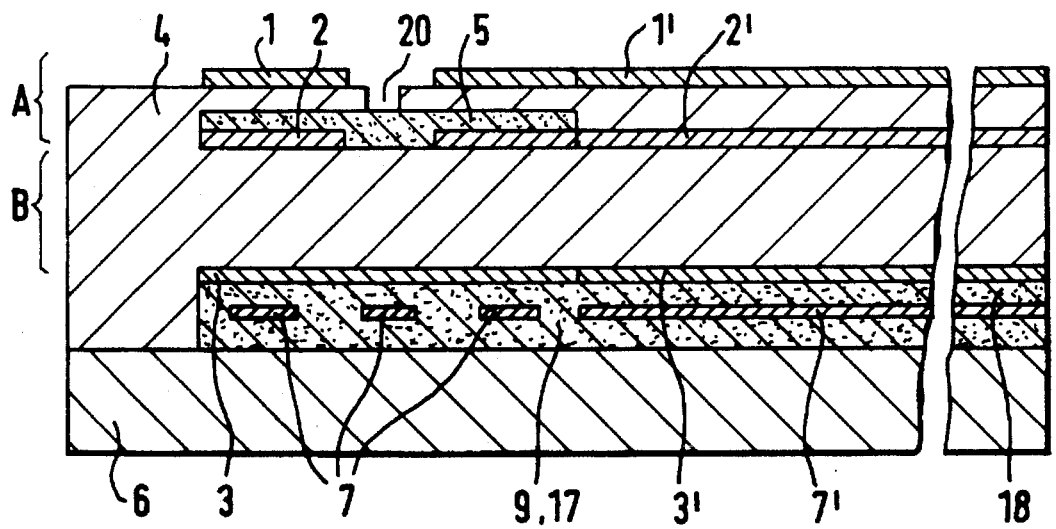
FIG. 5 shows a longitudinal section of a particularly advantageous embodiment of a measuring sensor according to the invention for which the control circuit also substantially corresponds to that shown in FIG. 1 but is not shown.

With the measuring sensors according to the invention, the oxygen content of exhaust gases from internal combustion engines can be determined in the rich, neutral and lean ranges, and the composition of the fuel-air mixture supplied to the engines can be controlled. As can be seen in FIGS. 1, 4 and 5, the measuring sensors include a measuring cell A and a reference cell B having porous electrodes 1 through 3, with electrode 2 being common to both cells. Electrodes 1 through 3 are connected to a fixed electrolyte 4. Exhaust gas is supplied to electrode 2 by way of a diffusion hole 20 and a diffusion barrier 5.

Electrodes 1 and 2, which are generally composed of platinum, are part of the measuring cell. They are advisably 0.5 to 2 µm thick and porous. Thicker electrodes impede the passage of the gases, and thus increase the time required by the sensors with respect to changes in the oxygen content of the exhaust gas.

Zirconium(IV) oxide, which is advantageously stabilized, advisably partially stabilized, by an oxide of the second subgroup of the periodic table of the elements, i.e., Group III B, is particularly suited as fixed electrolyte 4. Examples of suitable stabilizing oxides are scandium oxide and, preferably, yttrium oxide, as well as the oxides of the higher rare earth elements having an atomic number greater than 64, such as erbium oxide. The quantities which are optimal for partial stabilization can be determined experimentally without difficulty. For example, for the zirconium(IV) oxide/yttrium(III) oxide system, four to seven mol percent of yttrium (III) oxide provide good partial stabilization of the zirconium (IV) oxide. Other suitable, ion-conducting fixed electrolytes are mixed oxides of zirconium(IV) oxide with titanium(IV) oxide, bismuth(III) oxide and/or cerium(IV) oxide.

Diffusion barrier 5 is advisably composed of porous zirconium(IV) oxide, and generally has a thickness ranging between 15 and 45 µm. The diffusion barrier 5 causes current $I_M$ in measuring cell A to be exclusively determined by the diffusion process, and contributes to the maintenance of a constant oxygen partial pressure above electrode 2. During operation in the lean range, i.e., with oxygen-rich exhaust gases, diffusion barrier 5 primarily prevents the diffusion of oxygen to electrode 2. During operation in the rich range, i.e., with waste gases containing a large amount of non-burned portions and little oxygen, the barrier primarily prevents the diffusion of hydrocarbons, carbon monoxide and hydrogen, again to electrode 2. Diffusion barrier 5 must be of such a nature with regard to shape, size and porosity that the oxygen partial pressure corresponding to reference voltage $U_R$ can be established at electrode 2. In measuring sensors for determining oxygen in exhaust gases of internal combustion engines, the reference voltage $U_R$ is typically approximately 400 mV, which corresponds to an oxygen partial pressure of approximately $10^{-8}$ bar. This partial pressure is established when the engine is operated with lambda values of approximately one. If the diffusion resistance of the barrier layer is too low, too much oxygen reaches electrode 2 during operation in the lean range, so that measuring current $I_M$ is not voltage-independent (i.e., is not a limiting current) and is, thus, no longer a measure of the oxygen concentration in the exhaust gas, that is, of the lambda value. With too large a diffusion resistance, a limiting current flows that is, however, only small, so that the sensitivity of the measuring sensor leaves something to be desired.

Reference cell B is likewise a pump cell. Its electrode 3 is, again, generally composed of platinum. It is advisably likewise porous. The pores then define an oxygen reference zone 17. Its thickness advisably ranges from 5 to 25 µm. Electrode 3 is hermetically sealed against the exhaust gas and is connected to the atmosphere by way of a pressure-equalization line or connection 18. The oxygen pressure at electrode 3 is established at approximately one bar, because the oxygen pumped away from electrode 2 in ion form and developed in gaseous form at electrode 3 escapes into the environment through pressure-equalization line 18.

Measuring cell A and reference cell B can be connected as shown in FIGS. 1 and 4 to substrate 6, which is advisably composed of aluminum oxide. Connected to substrate 6 is a heating means 7, which is in turn protected by a cover 8, which again can be composed of aluminum oxide. It is, however, also possible to dispose the heating means between two layers of zirconium(IV) oxide in a conventional manner. Heating apparatus 7 heats the two cells to temperatures at which the ion conductivity of fixed electrolyte 4 is sufficiently high. These temperatures advantageously range from 550° to 800° C.

In a further embodiment of the measuring sensors of the invention which is shown in FIG. 5, electrode 3 and heating means 7 are spatially and functionally combined in a porous insulation 9. Together with the porous electrode 3, the porous insulation 9 of heating means 7, which is advisably composed of aluminum oxide, forms the internal oxygen reference zone 17 and, together with the porous electrode 3 in connection with a porous conductor track 3', forms pressure-equalization line or connection 18. The porous insulation 9 is covered with substrate 6 which, in this embodiment, also takes over the protective function of cover 8. As discussed previously, this embodiment offers advantages in terms of production technology.

As can be seen from the longitudinal sections shown in FIGS. 1 and 5, the signals of electrodes 1, 2 and 3 are conducted, by corresponding conductor tracks 1', 2' and 3', to the atmosphere-side end of the measuring sensor (see pressure equalization line or connection 18 in FIGS. 1 and 5), where they are guided to the surface of the measuring sensor by means of feedthroughs (not shown). Heating means 7 utilizes two supply lines, of which only the heater supply line 7' is shown, which are provided at the atmosphere-side end of the measuring sensor with line contacts (not shown). Conductor tracks 1', 2' and 3' can be guided in a known manner between the different sheets of fixed electrolyte 4 or substrate 6, to the atmosphere-side end, and configured there adjacent or opposite one another as contacts for each connection (not shown).

As mentioned, connected to electrode 3 is the porous conductor track 3', which, together with the porous electrode 3 and, if needed—as in FIG. 5—together with heater insulation 9, forms pressure-equalization line 18, through which the oxygen that has developed at electrode 3 escapes. For reasons of production technology, it is recommended to use the same material to produce electrode 3 and conductor track 3'. Then pores that permit an equalization of pressure with the atmosphere form, both in electrode 3 and in conductor track 3', during sintering. However, an open channel from electrode 3 to the atmosphere-side end of the measuring sensor can also be provided, by a porous, non-conductive material which differs from the electrode material, such as aluminum oxide. In such a case, however, a separate conductor track 3' that conducts the signal of electrode 3 to the evaluating circuit must be created.

The measuring cell and the reference cell are advisably connected by means of a control circuit, as represented schematically in FIG. 1. The control circuit is operated with a supply voltage $U_V^-$ from voltage source 10. When the measuring sensor is used to determine the oxygen content in exhaust gases of internal combustion engines, the battery of the motor vehicle is advisably the voltage source 10. A current source 12 supplies a constant pumping current $I_P$ for reference cell B that can be, for example, 50 microamperes. Moreover, a reference voltage source 12 that supplies reference voltage $U_R$ is present. When used in internal combustion engines, this voltage is generally approximately 400 mV. It is possible, however, to preset a different reference voltage $U_R$ that corresponds to the electric motor power when lambda equals one with the given ratios, for example, a voltage ranging between 300 and 800 mV. The reference voltage is applied to the input of an operational amplifier 13. An inverting input of operational amplifier 13 is connected to electrode 3 and current source 11.

If the oxygen partial pressure at electrode 2 changes across diffusion barrier 5 when the mixture changes, pumping voltage $U_P$ between electrode 2 and electrode 3 also changes. With a change into the rich range, according to FIG. 3, pumping voltage $U_P$ increases. With a change into the lean range, on the other hand, pumping voltage $U_P$ sinks below the value of approximately 400 mV, which corresponds to lambda= 1. Pumping voltage $U_P$ is present, as mentioned, at the inverting end of operational amplifier 13. Operational amplifier 13, operating as a difference amplifier, compares reference voltage $U_R$ with pumping voltage $U_P$ present at the inverting input. The result is that, with a rich gas mixture at the output of operational amplifier 13, a negative voltage potential having a corresponding measuring voltage $U_M$ is present, which drives a measuring current $I_M$ in such a way that oxygen is pumped in ion form from electrode 1 to electrode 2.

With a lean mixture, on the other hand, measuring voltage $U_M$ is present at the output of operational amplifier 13, along with a positive voltage potential, by means of which the flow direction of the measuring current reverses, and oxygen ions are transported from electrode 2 to electrode 1. The output of operational amplifier 13 is connected to electrode 1 by way of an ammeter 14. The measuring current, or limiting current, $I_M$ is measured with ammeter 14. Measuring voltage $U_M$ can be tapped between electrodes 1 and 2 by means of voltage measuring apparatus 15, and pumping voltage $U_P$ can be measured between electrodes 2 and 3 by means of a second voltage measuring apparatus 16. In place of ammeter 14, a measuring apparatus can alternatively be connected which supplies the current values of measuring current $I_M$ to a control apparatus in order to control the composition of the fuel-air mixture for an internal combustion engine.

The control circuit ensures that a constant, low oxygen partial pressure, advisably approximately $10^{-8}$ bar, is maintained above electrode 2. It is determined by the predetermined reference voltage $U_R$. This pressure is known to correspond approximately to the oxygen partial pressure in the exhaust gas in a stoichiometric fuel/air ratio. During operation in the lean range, the oxygen partial pressure is higher above electrode 2, despite diffusion barrier 5. Therefore, voltage $U_M$ of the measuring cell is increased, and oxygen is cathodically reduced and pumped in ion form to electrode 1, and discharged there:

$$\tfrac{1}{2}O_2 + 2e^- \rightarrow O^{2-}$$

(reaction at electrode 2 as cathode with a lean mixture)

$$O^{2-} \rightarrow \tfrac{1}{2}O_2 + 2e^-$$

(reaction at electrode 1 as anode with a lean mixture).

Depending on the oxygen component in the exhaust gas, more or less oxygen must be pumped in ion form from electrode 2 to electrode 1 when an oxygen partial pressure of approximately $10^{-8}$ bar is to be maintained at electrode 2. This occurs by means of changing pumping voltage $U_M$, which is predetermined by the operational amplifier based on the comparison of pumping voltage $U_P$ with reference voltage $U_R$. The current intensity $I_M$ in the measuring cell is correspondingly higher or lower. Current intensity $I_M$ is an important variable because it is the measure for the oxygen content in the exhaust gas, that is, current intensity $I_M$ is directly proportional to the oxygen content.

During operation in the rich range, that is, with an oxygen partial pressure of approximately $10^{-20}$ bar in the exhaust gas, the oxygen partial pressure at electrode 2 would be of the same magnitude. Therefore, oxygen must be pumped in ion form from electrode 1 to electrode 2 when an oxygen partial pressure of approximately $10^{-8}$ bar is to be maintained there:

$$CO_2 + 2e^- \rightarrow CO + O^{2-}$$

$$H_2O + 2e^- \rightarrow H_2 + O^{2-}$$

(reaction at electrode 1 as cathode with a rich mixture).

On the one hand, the oxygen ions oxidize the diffusing, oxidizable components at electrode 2, for example:

$$CO + O^{2-} \rightarrow CO_2 + 2e^-$$

$$H_2 + O^{2-} \rightarrow H_2O + 2e^-$$

$$C_2H_4 + 6\,O^{2-} \rightarrow 2\,CO_2 + 2\,H_2O + 12\,e^-$$

(reaction at electrode 2 as anode with a rich mixture).

On the other hand, oxygen ions are discharged to become molecular oxygen until the oxygen partial pressure (e.g., 10 bar) predetermined by reference voltage $U_R$ (e.g., 400 mV) has been achieved:

$$O^{2-} \rightarrow \tfrac{1}{2}O_2 + 2e^-$$

(reaction at electrode 2 as anode with a rich mixture).

With an appropriate diffusion barrier 5, a limiting current flows because all diffusing, oxidizable components are oxidized and elementary oxygen is only developed until the predetermined partial pressure is reached.

As explained, the control circuit causes the polarities of electrodes 1 and 2 to change poles when the quality of the exhaust gas changes, i.e., its composition changes from the lean to the rich range, or vice versa.

Figure 2:
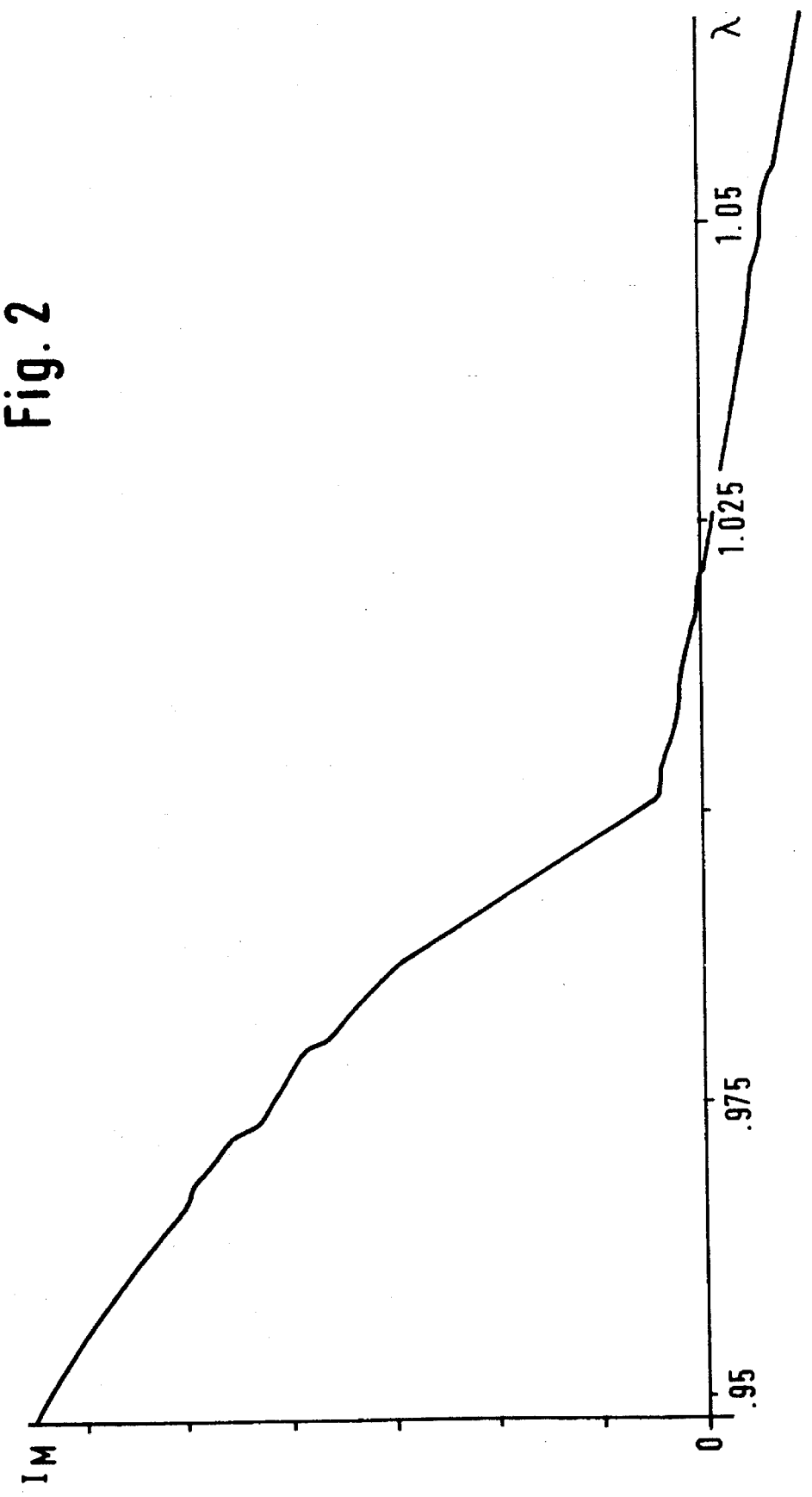
FIG. 2 shows a characteristic curve of such a measuring sensor, namely, the dependency of the lambda value on the pump flow $I_M$ in the measuring cell.
Figure 3:
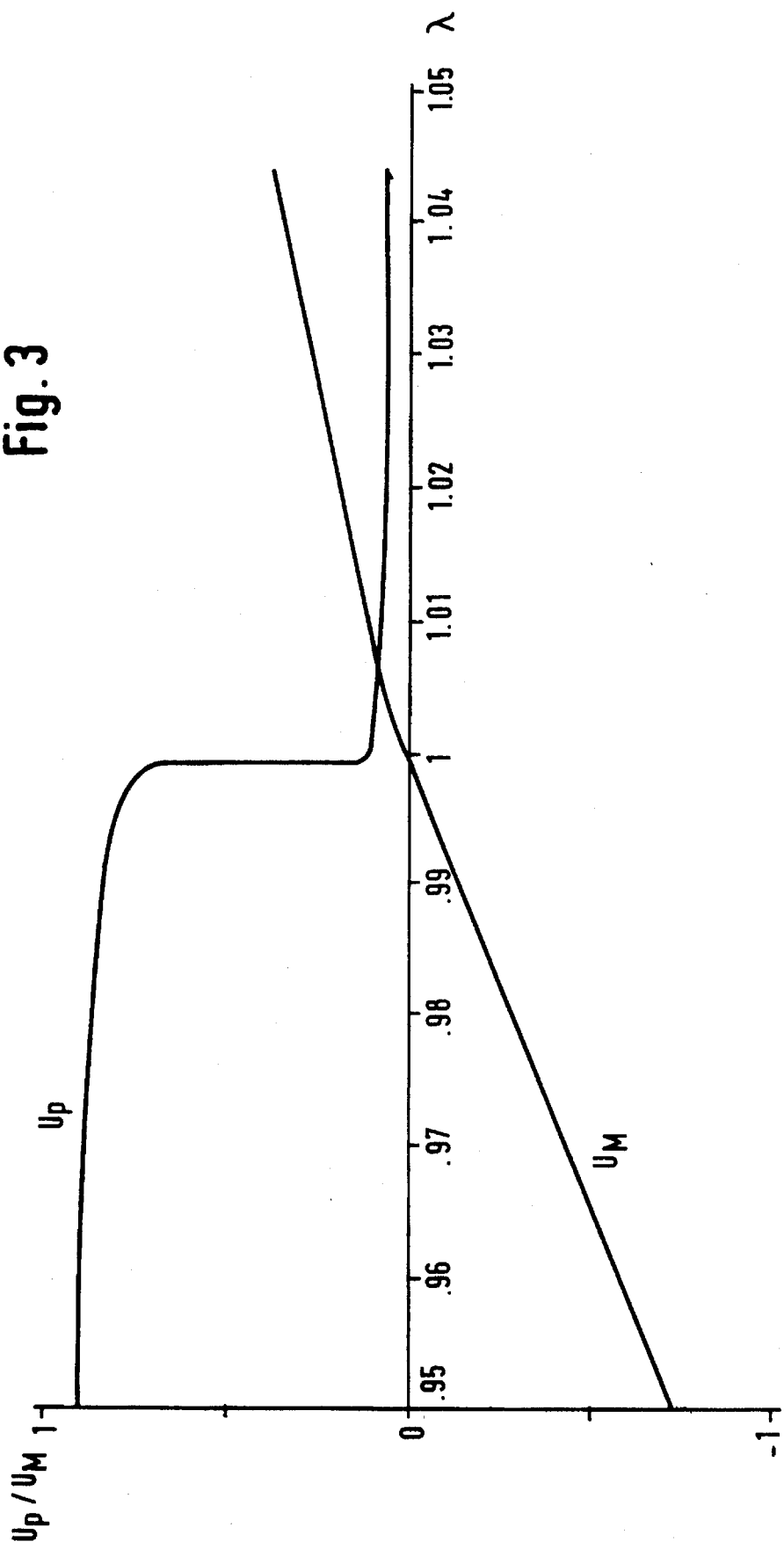
FIG. 3 shows two further characteristic curves of a measuring sensor according to the invention, namely, pumping voltage $U_P$ of reference cell B as a function of the lambda value, as would result without controlling intervention, with a compensated measuring voltage $U_M$ derived from pump flow $I_M$ of the measuring cell plotted against the lambda value.

The relationship of polarity, lambda value, pumping voltage $U_M$ and current intensity $I_M$ is demonstrated in FIG. 3 in which the characteristic curve of the reference cell (voltage $U_P$ against lambda value) and the characteristic curve of the measuring cell (pumping voltage $U_M$ of the measuring cell against lambda value) are plotted. When the internal combustion engine is operated with a stoichiometric fuel-air mixture, that is, the lambda value is one, pumping voltage $U_M$ in the measuring cell is practically 0 V, and the voltage in the reference cell is approximately 400 mV. If the composition of the exhaust gas changes in the direction of the lean range, for example, to lambda=1.04, small shifts in the lambda value lead to a significant reduction in voltage $U_P$. The control circuit thereupon switches electrode 1 to be the anode and electrode 2 to be the cathode. Voltage $U_P$ in the measuring cell is increased and oxygen is pumped in ion form away from electrode 2 until the oxygen partial pressure above electrode 2 is again approximately $10^{-8}$ bar, and voltage $U_M$ in the measuring cell is again approximately 400 mV. As long as the composition of the exhaust gas does not change, oxygen must be pumped off in ion form, and a corresponding current $I_M$ flows whose intensity can be read from FIG. 2 and which, in connection with the polarity of electrodes 1 and 2, is proportional to the oxygen content of the exhaust gas.

If the composition of the exhaust gas shifts in the direction of lambda=1, for example, to lambda=1.02, current intensity $I_M$ is reduced corresponding to the lower oxygen content of the waste gas, but the polarity of electrodes 1 and 2 is maintained. Not until the lambda value changes to less than one, for example, to 0.99, does the then-occurring leap of variable $U_P$ from, for example, approximately 400 mV to approximately 960 mV cause the control circuit to change the poles of electrodes 1 and 2 and, by means of a corresponding change in pumping voltage $U_M$, to pump oxygen in the form of ions from electrode 1 to electrode 2. The current intensity $I_M$ corresponding to the ion flow is maintained provided that the oxygen content in the exhaust gas does not change, and is, again in connection with the polarity of the two electrodes, a measure for the oxygen content of the exhaust gas.

FIG. 4 shows an advantageous embodiment of an exhaust gas sensor according to the invention in which the number of connections is reduced to four. This is achieved in that pumping current $I_P$ of reference cell B is detected at the heating connections by means of a series resistor 21—advisably printed onto the exhaust gas sensor—with a magnitude of 100 k$\Omega$. Pumping voltage $I_P$ then remains nearly constant because of the changing voltage at the heating unit. It continues to be ensured, however, that an oxygen pressure of approximately one bar is established in electrode 3, so that it can serve as a reference electrode.

The exhaust gas sensors according to the invention are manufactured in a known manner in accordance with conventional methods. Substrate 6 and cover 8 can be produced from sheets and the electrodes can be printed on or applied in accordance with any other of the well known methods in the art. Fixed electrolyte 4 and diffusion barrier layer 5 are advisably applied by means of screen printing. After construction of the sensor from the individual components, the components are fixedly connected to one another by means of co-sintering, advisably at temperatures ranging from about 1200° to about 1450° C. No representation of insulating layers for the conductor tracks is shown in FIGS. 1, 4 and 5. These insulating layers are necessary so that the conductor tracks do not function as additional electrodes. A person skilled in the art would be well aware of where and how to insulate electrodes.

The invention has been described in detail with respect to preferred embodiments, and it will now be apparent from the foregoing to those skilled in the art that changes and modifications may be made without departing from the invention and its boarder aspects, and the invention, therefore, in the appended claims is intended to cover all such changes and modifications as fall within the true spirit of the invention.

What is claimed is:

1. A measuring sensor for determining the oxygen content in a gas mixture including an exhaust gas mixture from an internal combustion engine, comprising:
   a. an electrochemical measuring cell (A) having a pair of electrodes;
   b. an electrochemical reference cell (B) having a pair of electrodes, one of which pair of electrodes is common to the electrochemical reference cell (B) and the electrochemical measuring cell (A), and having defined therein an internal oxygen reference zone which is hermetically sealed against the gas mixture and is connected to the atmosphere by way of a pressure-equalization line which permits escape into the atmosphere of excess oxygen;
   c. a diffusion barrier which impedes the diffusion of the gas mixture to the electrode which is common to the electrochemical reference cell (B) and the electrochemical measuring cell (A);
   d. a fixed electrolyte provided between the electrochemical measuring cell (A) and the electrochemical reference cell (B);
   e. a heating means for heating the electrochemical measuring cell (A) and the electrochemical reference cell (B) to a temperature at which the fixed electrolyte has an ionic conductivity effective to enable the measuring sensor to determine the oxygen content in the gas mixture; and
   f. a control circuit which is comprised of:
      (1) a voltage source which supplies a supply voltage ($U_V$);
      (2) a current source which maintains a constant pumping current ($I_P$) in the electrochemical reference cell (B);
      (3) a reference voltage source which can be set at a reference voltage ($U_R$) which is specific and constant; and
      (4) circuit means comprising an operational amplifier which compares a pumping voltage ($U_P$) present between the pair of electrodes of the electrochemical reference cell (B) with the reference voltage ($U_R$), which is connected to the electrodes of the electrochemical measuring cell (A) and the electrochemical reference cell (B), and which supplies an output signal which keeps the oxygen partial pressure at the electrode which is common at least approximately constant, and supplies a limiting current, $I_M$, to the electrochemical measuring cell (A), which limiting current, $I_M$, is used as a measuring signal for the oxygen content of the gas mixture.

2. The measuring sensor as defined in claim 1, further comprising a porous conductor track in communication with the atmosphere and in communication with the internal oxygen reference zone so that the internal oxygen reference zone and the porous conductor track together form the pressure-equalization line.

3. The measuring sensor as defined in claim 2, wherein the electrode of the electrochemical reference cell (B), which is not in common with the electrochemical measuring cell (A), is porous, and the pores define the internal oxygen reference zone.

4. The measuring sensor as defined in claim 3, wherein porous insulation is disposed in the vicinity of the porous electrode of the electrochemical reference cell (B), which is not in common with the electrochemical measuring cell (A), and wherein the heating means is imbedded in the porous insulation which forms, together with the porous electrode, the internal oxygen reference zone and, together with the porous electrode and the porous conductor track, forms the pressure-equalization line.

5. The measuring sensor as defined in claim 4, wherein the porous insulation is composed of aluminum oxide.

6. The measuring sensor as defined in claim 1, wherein the fixed electrolyte of the electrochemical measuring cell (A) and the electrochemical reference cell (B) is composed of zirconium (IV) oxide which is at least partially stabilized.

7. In an internal combustion engine, the improvement comprising:

a measuring sensor according to claim 1 for determining the oxygen content of exhaust gas mixtures from the internal combustion engine whereby the fuel-air mixture's composition being supplied to the internal combustion engine is controlled in response to the oxygen content measured by the measuring sensor.

8. The process of controlling a fuel-air mixture's composition being supplied to an internal combustion engine, comprising:

providing the internal combustion engine with a measuring sensor according to claim 1 for determining the oxygen content of exhaust gas mixtures from the internal combustion engine; and controlling the fuel-air mixture's composition being supplied to the internal combustion engine in response to the oxygen content measured by the measuring sensor.

9. The process as defined in claim 8, wherein the reference voltage ($U_R$) is set at a value of about 400 mV.

* * * * *